United States Patent
Carlson et al.

(10) Patent No.: US 7,780,606 B2
(45) Date of Patent: *Aug. 24, 2010

(54) HEMODYNAMIC STABILITY ASSESSMENT BASED ON HEART SOUNDS

(75) Inventors: Gerrard M. Carlson, Champlin, MN (US); Yayun Lin, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 308 days.

This patent is subject to a terminal disclaimer.

(21) Appl. No.: 11/277,773

(22) Filed: Mar. 29, 2006

(65) Prior Publication Data

US 2007/0239218 A1    Oct. 11, 2007

(51) Int. Cl.
*A61B 5/02* (2006.01)
(52) U.S. Cl. ........................................ 600/508; 600/515
(58) Field of Classification Search ............... 607/4, 607/14, 17–19, 2, 5, 6, 7, 9, 11, 23; 600/528
See application file for complete search history.

(56) References Cited

U.S. PATENT DOCUMENTS

| | | |
|---|---|---|
| 4,094,308 A | 6/1978 | Cormier |
| 4,289,141 A | 9/1981 | Cormier |
| 4,291,699 A | 9/1981 | Geddes et al. |
| 4,428,378 A | 1/1984 | Anderson et al. |
| 4,428,380 A | 1/1984 | Wong et al. |
| 4,446,872 A | 5/1984 | Marsoner et al. |
| 4,548,204 A | 10/1985 | Groch et al. |
| 4,586,514 A | 5/1986 | Schlager et al. |
| 4,628,939 A | 12/1986 | Little et al. |
| 4,649,930 A | 3/1987 | Groch et al. |
| 4,763,646 A | 8/1988 | Lekholm |
| 4,905,706 A | 3/1990 | Duff et al. |
| 4,915,113 A | 4/1990 | Holman |
| 4,967,760 A | 11/1990 | Bennett, Jr. et al. |
| 4,981,139 A | 1/1991 | Pfohl |
| 4,989,611 A | 2/1991 | Zanetti et al. |

(Continued)

FOREIGN PATENT DOCUMENTS

EP    0467695 A2    1/1992

(Continued)

OTHER PUBLICATIONS

"PCT Application No. PCT/US2007/006345, International Search Report mailed Oct. 24, 2007", 6 pgs.

(Continued)

*Primary Examiner*—Carl H Layno
*Assistant Examiner*—Gary A Porter, Jr.
(74) *Attorney, Agent, or Firm*—Schwegman, Lundberg & Woessner, P.A.

(57) ABSTRACT

A system comprising an implantable medical device (IMD). The IMD includes an implantable sensor operable to produce an electrical signal representative of mechanical activity of a heart of a subject and a controller circuit coupled to the sensor. The IMD also includes a heart sound sensor interface circuit to produce a heart sound signal, a tachyarrhythmia detector, and a controller circuit. The controller circuit includes a hemodynamic stability assessment module configured to determine that at least one episode of ventricular tachyarrhythmia is detected in a subject and obtain a measurement of hemodynamic stability of the ventricular tachyarrhythmia from the heart sound signal.

17 Claims, 11 Drawing Sheets

U.S. PATENT DOCUMENTS

| | | |
|---|---|---|
| 5,010,889 A | 4/1991 | Bredesen et al. |
| 5,012,815 A | 5/1991 | Bennett, Jr. et al. |
| 5,025,809 A | 6/1991 | Johnson et al. |
| 5,040,533 A | 8/1991 | Fearnot |
| 5,137,019 A | 8/1992 | Pederson et al. |
| 5,159,932 A | 11/1992 | Zanetti et al. |
| 5,168,869 A | 12/1992 | Chirife |
| 5,179,947 A | 1/1993 | Meyerson et al. |
| 5,218,969 A | 6/1993 | Bredesen et al. |
| 5,292,341 A | 3/1994 | Snell |
| 5,301,679 A | 4/1994 | Taylor |
| 5,305,745 A | 4/1994 | Zacouto |
| 5,321,618 A | 6/1994 | Gessman |
| 5,334,222 A | 8/1994 | Salo et al. |
| 5,337,752 A | 8/1994 | Reeves |
| 5,365,932 A | 11/1994 | Greenhut |
| 5,391,190 A | 2/1995 | Pederson et al. |
| 5,411,531 A * | 5/1995 | Hill et al. ................. 607/14 |
| 5,417,717 A | 5/1995 | Salo et al. |
| 5,472,453 A | 12/1995 | Alt |
| 5,496,361 A | 3/1996 | Moberg et al. |
| 5,514,163 A | 5/1996 | Markowitz et al. |
| 5,549,650 A | 8/1996 | Bornzin et al. |
| 5,554,177 A | 9/1996 | Kieval et al. |
| 5,593,431 A | 1/1997 | Sheldon |
| 5,609,612 A | 3/1997 | Plicchi et al. |
| 5,628,777 A | 5/1997 | Moberg et al. |
| 5,674,256 A | 10/1997 | Carlson |
| 5,685,317 A | 11/1997 | Sjostrom |
| 5,687,738 A | 11/1997 | Shapiro et al. |
| 5,693,075 A | 12/1997 | Plicchi et al. |
| 5,697,375 A | 12/1997 | Hickey |
| 5,700,283 A | 12/1997 | Salo |
| 5,720,771 A | 2/1998 | Snell |
| 5,725,562 A | 3/1998 | Sheldon |
| 5,759,199 A | 6/1998 | Snell et al. |
| 5,792,195 A | 8/1998 | Carlson et al. |
| 5,836,987 A | 11/1998 | Baumann et al. |
| 5,860,933 A | 1/1999 | Don Michael |
| 5,935,081 A | 8/1999 | Kadhiresan |
| 5,951,593 A * | 9/1999 | Lu et al. ................. 607/14 |
| 5,991,661 A | 11/1999 | Park et al. |
| 6,009,349 A | 12/1999 | Mouchawar et al. |
| 6,015,388 A | 1/2000 | Sackner et al. |
| 6,026,324 A | 2/2000 | Carlson |
| 6,044,297 A | 3/2000 | Sheldon et al. |
| 6,044,298 A | 3/2000 | Salo et al. |
| 6,044,299 A | 3/2000 | Nilsson |
| 6,045,513 A | 4/2000 | Stone et al. |
| 6,048,319 A * | 4/2000 | Hudgins et al. ............. 600/528 |
| 6,053,872 A | 4/2000 | Mohler |
| 6,058,329 A | 5/2000 | Salo et al. |
| 6,064,910 A | 5/2000 | Andersson et al. |
| 6,115,628 A | 9/2000 | Stadler et al. |
| 6,128,526 A | 10/2000 | Stadler et al. |
| 6,144,880 A | 11/2000 | Ding et al. |
| 6,152,884 A | 11/2000 | Bj.o slashed.rgaas |
| 6,190,324 B1 | 2/2001 | Kieval et al. |
| 6,193,668 B1 | 2/2001 | Chassaing et al. |
| 6,208,900 B1 | 3/2001 | Ecker et al. |
| 6,208,901 B1 | 3/2001 | Hartung |
| 6,264,611 B1 | 7/2001 | Ishikawa et al. |
| 6,273,856 B1 | 8/2001 | Sun et al. |
| 6,275,727 B1 | 8/2001 | Hopper et al. |
| 6,298,269 B1 | 10/2001 | Sweeney |
| 6,304,773 B1 | 10/2001 | Taylor et al. |
| 6,351,672 B1 | 2/2002 | Park et al. |
| 6,351,673 B1 | 2/2002 | Ding et al. |
| 6,366,811 B1 | 4/2002 | Carlson |
| 6,368,283 B1 | 4/2002 | Xu et al. |
| 6,368,284 B1 | 4/2002 | Bardy |
| 6,409,675 B1 | 6/2002 | Turcott |
| 6,415,033 B1 | 7/2002 | Halleck et al. |
| 6,440,082 B1 | 8/2002 | Joo et al. |
| 6,459,929 B1 | 10/2002 | Hopper et al. |
| 6,466,821 B1 | 10/2002 | Pianca et al. |
| 6,477,406 B1 | 11/2002 | Turcott |
| 6,478,746 B2 | 11/2002 | Chassaing et al. |
| 6,480,733 B1 | 11/2002 | Turcott |
| 6,496,715 B1 | 12/2002 | Lee et al. |
| 6,520,924 B2 | 2/2003 | Lee |
| 6,527,729 B1 | 3/2003 | Turcott |
| 6,542,775 B2 | 4/2003 | Ding et al. |
| 6,575,916 B2 | 6/2003 | Halleck et al. |
| 6,625,493 B2 | 9/2003 | Kroll et al. |
| 6,626,842 B2 | 9/2003 | Oka |
| 6,643,548 B1 | 11/2003 | Mai et al. |
| 6,645,145 B1 | 11/2003 | Dreschel et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,684,103 B2 | 1/2004 | Ding et al. |
| 6,733,464 B2 | 5/2004 | Olbrich et al. |
| 6,788,970 B1 | 9/2004 | Park et al. |
| 6,792,308 B2 | 9/2004 | Corbucci |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,845,263 B2 | 1/2005 | Kawaguchi |
| 7,043,305 B2 | 5/2006 | Kenknight et al. |
| 7,139,609 B1 | 11/2006 | Min et al. |
| 7,194,306 B1 | 3/2007 | Turcott |
| 7,248,923 B2 | 7/2007 | Maile et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0045805 A1 | 3/2003 | Sheldon et al. |
| 2003/0055352 A1 | 3/2003 | Hayek et al. |
| 2003/0055461 A1 | 3/2003 | Girouard et al. |
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105496 A1 | 6/2003 | Yu et al. |
| 2003/0120159 A1 | 6/2003 | Mohler |
| 2003/0144702 A1 | 7/2003 | Yu et al. |
| 2003/0144703 A1 | 7/2003 | Yu et al. |
| 2003/0158492 A1 | 8/2003 | Sheldon et al. |
| 2003/0158584 A1 | 8/2003 | Cates et al. |
| 2003/0171791 A1 | 9/2003 | KenKnight et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler et al. |
| 2003/0233132 A1 | 12/2003 | Pastore et al. |
| 2004/0002739 A1 | 1/2004 | Cates et al. |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0176810 A1 | 9/2004 | Stadler et al. |

| | | | |
|---|---|---|---|
| 2004/0215264 A1 | 10/2004 | Van Bentem | |
| 2004/0215265 A1 | 10/2004 | Keizer | |
| 2004/0225332 A1 | 11/2004 | Gebhardt et al. | |
| 2004/0236239 A1 | 11/2004 | Murray et al. | |
| 2004/0254481 A1 | 12/2004 | Brodnick | |
| 2004/0267147 A1 | 12/2004 | Sullivan | |
| 2004/0267148 A1 | 12/2004 | Arand et al. | |
| 2005/0027323 A1 | 2/2005 | Mulligan et al. | |
| 2005/0033190 A1 | 2/2005 | Bauer | |
| 2005/0060001 A1 | 3/2005 | Singhal et al. | |
| 2005/0102001 A1 | 5/2005 | Maile et al. | |
| 2005/0148896 A1 | 7/2005 | Siejko et al. | |
| 2005/0149136 A1 | 7/2005 | Siejko et al. | |
| 2006/0020294 A1 | 1/2006 | Brockway et al. | |
| 2006/0025699 A1 | 2/2006 | Maile et al. | |
| 2006/0030892 A1 | 2/2006 | Kadhiresan et al. | |
| 2006/0041280 A1 | 2/2006 | Stahmann et al. | |
| 2006/0161070 A1 | 7/2006 | Siejko et al. | |
| 2007/0149890 A1* | 6/2007 | Li et al. | 600/515 |
| 2008/0015652 A1 | 1/2008 | Maile et al. | |
| 2009/0287106 A1 | 11/2009 | Zhang et al. | |

FOREIGN PATENT DOCUMENTS

| | | |
|---|---|---|
| EP | 0474958 | 3/1992 |
| EP | 0709058 A1 | 5/1996 |
| WO | WO-0156651 A1 | 8/2001 |
| WO | WO-03041797 A2 | 5/2003 |
| WO | WO-2004/012815 A1 | 2/2004 |
| WO | WO-2004/060483 A1 | 7/2004 |
| WO | WO-2005/122902 A1 | 12/2005 |
| WO | WO 2007/126578 A2 | 11/2007 |

OTHER PUBLICATIONS

"PCT Application No. PCT/US2007/006345, Written Opinion mailed Oct. 24, 2007", 8 pgs.
"U.S. Appl. No. 10/334,694 Non-Final Office Action mailed Mar. 19, 2008", 15 pgs.
Rosa, A. , et al., "Ectopic Pacing at Physiological Rate Improves Postanoxic Recovery of the Developing Heart", *Am. J. Physiol. —Heart Circ. Physiol.*, 284, (2003), H2384-H2392.
U.S. Appl. No. 10/334,694, filed Dec. 30, 2002, Method and Apparatus for Monitoring of Diastolic Hemodynamics.
U.S. Appl. No. 10/746,874, filed Dec. 24, 2003, A Third Heart Sound Activity Index for Heart Failure Monitoring.
U.S. Appl. No. 10/703,175, filed Nov. 6, 2003, A Dual-Use Sensor for Rate Responsive Pacing and Heart Sound Monitoring.
U.S. Appl. No. 10/900,570, filed Jul. 28, 2004, Determining a Patient's Posture From Mechanical Vibrations of the Heart.
U.S. Appl. No. 11/037,275, filed Jan. 18, 2005, Method for Correction of Posture Dependence on Heart Sounds.
U.S. Appl. No. 11/148,107, filed Jun. 8, 2005, Ischemia Detection Using Heart Sound Sensor.
U.S. Appl. No. 11/129,050, filed May 13, 2005, Method and Apparatus for Cardiac Protection Pacing.
U.S. Appl. No. 11/465,878, filed Aug. 21, 2006, A Third Heart Sound Activity Index for Heart Failure Monitoring.
Baynham, Tamara C., et al., "Method and Apparatus for Cardiac Protection Pacing", U.S. Appl. No. 11/129,050, filed May 13, 2005, 33 Pages.
Brockway, Marina, et al., "Method and Apparatus for Monitoring Heart Failure Patients With Cardiopulmonary Comorbidities", U.S. Appl. No. 10/897,856, filed Jul. 23, 2004, 54 pages.
Bulgrin, J. R., et al., "Comparison of Short-Time Fourier, Wavelet and Time-Domain Analyses of Intracardiac Sounds", *Biomedical Sciences Instrumentation*, 29, (1993), 465-472.
Ji, J., "An Ultraminiature CMOS Pressure Sensor for a Multiplexed Cardiovascular Catheter", IEEE Transactions on Electron Devices, vol. 39, No. 10, (Oct. 1992), pp. 2260-2267.
Kinderman, Michael, et al., "Optimizing the AV Delay in DDD Pacemaker Patients with High Degree AV Block: Mitral Valve Doppler Versus Impedance Cardiography", *PACE*, vol. 20, pp. 2453-2462, (Oct. 1997), 2453-2462.

Konta, Tsuyoshi, et al., "Significance of Discordant ST Alternans in Ventricular Fibrillation", *Circulation*, 82(6), (Dec. 1990), 2185-2189
Krayenbuhl, H. P., "Hemodynamics in ischemia. Systolic phase", *Z. Kardiol.*, 73 Suppl 2, [Article in German], (1984), 119-25.
Leatham, A., "Splitting of the First and Second Heart Sounds", *Lancet*, 267 (6839), (Sep. 25, 1954), 607-614.
Makhoul, John, "Linear Prediction: A Tutorial Review", *Proceedings of the IEEE*, 63, (Apr. 1975), 561-580.
Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s,(1992), 856-862.
Panju, Akbar A., et al., "Is This Patient Having a Mycardial Infraction?", *The Rational Clinical Examination*, JAMA, vol. 280, No. 14, (Oct. 14, 1998), 1256-1263.
Ritter, P., et al., "A Built-In System Based on the Peak Endocardial Acceleration (PEA) for AV-Delay Optimization in DDDR Pacing", *PACE*, 20(5) (Part II), (Abstract of Paper presented at EUROPACE '97),(May 1997), p. 1567.
Rubenstein, Donald S., et al., "Premature Beats Elicit a Phase Reversal of Mechanoelectrical Alternans in Cat Ventricular Myocytes", *Circulation*, vol. 91, No. 1, Jan. 1995, American Heart Association,(Jan. 1, 1995), 201-214.
Salerno, D. M., "Seismocardiography for monitoring changes in left ventricular function during ischemia.", *Chest*, 100(4), (Oct. 1991), 991-3.
Siejko, Krzysztof Z., et al., "A Third Heart Sound Activity Index Monitoring", U.S. Appl. No. 11/465,878, filed Aug. 21, 2006, 35 Pages.
Smith, Damon, et al., "Influence of the Aortic Component of the Second Heart Sound on Left Ventricular Maximal Negative dP/dt in the Dog", *Am. J. Cardiol.*, 55:205, (1985), 205-209.
Stein, Emanuel, et al., "Rapid Interpretation of Heart Sounds and Murmurs", Baltimore: Williams & Wilkins, 4th ed., (1997), 85-105.
Tavel, Morton E., "The Appearance of Gallop Rhythm after Exercise Stress Testing", *Clin. Cardiol.*, vol. 19, (1996), 887-891.
Wariar, R., et al., "Systems and Methods for Multi-Axis Cardiac Vibration Measurements", U.S. Appl. No. 11/135,985, filed May 24, 2004.
Wood, J.C., et al., "Time-Frequency Transforms: A New Approach to First Heart Sound Frequency Dynamics", *IEEE Transactions on Biomedical Engineering*, 39 (7), US, (Jul. 1, 1992), 730-740.
Zhang, Y., et al., "Ischemia Detection Using a Heart Sound Sensor", U.S. Appl. No. 11/148,107, filed Jun. 8, 2005, 41 pgs.
"U.S. Appl. No. 10/334,694, Final Office Action mailed Oct. 7, 2008", 14 pgs.
"U.S. Appl. No. 10/334,694, Response filed Jun. 19, 2008 to Non-Final Office Action mailed Mar. 19, 2008", 20 pgs.
"U.S. Appl. No. 11/037,275 Final Office Action mailed Jun. 17, 2008", 13 pgs.
"U.S. Appl. No. 11/037,278 Response filed Sep. 17, 2008 to Final Office Action mailed Jun. 17, 2008", 12 pages.
"U.S. Appl. No. 11/129,050, Advisory Action mailed Jul. 28, 2008", 3 pgs.
"U.S. Appl. No. 11/129,050, Response filed Jul. 14, 2008 to Final Office Action mailed May 12, 2008", 13 pgs.
"U.S. Appl. No. 11/129,050 Response filed Sep. 12, 2008 to Advisory Action mailed Jul. 28, 2008", 12 pgs.
"U.S. Appl. No. 11/148,107 Restriction Requirement mailed May 30, 2008", 6 pgs.
"U.S. Appl. No. 11/148,107, Response filed Oct. 20, 2008 to Non-Final Office Action mailed Jul. 18, 2008", 9 pgs.
"U.S. Appl. No. 11/148,107, Non-Final Office Action mailed Jul. 18, 2008", 8 pgs.
"U.S. Appl. No. 11/148,107, Response filed Jun. 30, 2008 to Restriction Requirement mailed May 30, 2008", 7 pgs.
"U.S. Appl. No. 10/900,570, Non-Final Action mailed Jul. 25, 2008", 5 pgs.
"U.S. Appl. No. 10/334,694, Response filed Dec. 8, 2008 to Final Office Action mailed Oct. 7, 2008", 18 pgs.
"U.S. Appl. No. 10/334,694, Advisory Action mailed Dec. 23, 2008", 3 pgs.

"U.S. Appl. No. 10/334,694, Non-Final Office Action mailed Mar. 18, 2009", 15 pgs.

"U.S. Appl. No. 10/746,874, Response filed Apr. 17, 2006 to Restriction Requirement mailed Mar. 31, 2006", 14 pgs.

"U.S. Appl. No. 10/746,874, Restriction Requirement mailed Mar. 31, 2006", 6 pgs.

"U.S. Appl. No. 10/900,570, Response filed Nov. 25, 2008 to Non-Final Office Action mailed Jul. 25, 2008", 9 pages.

"U.S. Appl. No. 10/900,570, Notice of Allowance mailed Mar. 6, 2009", 6 pgs.

"U.S. Appl. No. 11/037,275, Non-Final Office Action mailed Jan. 15, 2009", 9 pgs.

"U.S. Appl. No. 11/129,050, Response filed Feb. 23, 2009 to Non Final Office Action mailed Nov. 6, 2008", 13 pgs.

"U.S. Appl. No. 11/129,050, Non-Final Office Action mailed Nov. 6, 2008", 8 pgs.

"U.S. Appl. No. 11/148,107, Final Office Action mailed Jan. 14, 2009", 10 pgs.

"U.S. Appl. No. 11/148,107, Response filed Mar. 16, 2009 to Final Office Action mailed Jan. 14, 2009", 9 pages.

"U.S. Appl. No. 11/113,828, Non-Final Office Action mailed Mar. 5, 2008", 9 pgs.

"U.S. Appl. No. 10/334,694, Response filed Jul. 17, 2009 to Non Final Office Action mailed Mar. 18, 2009", 18 pgs.

"U.S. Appl. No. 11/148,107, Notice of Allowance mailed Mar. 30, 2009", 4 pgs.

"U.S. Appl. No. 10/334,694 Final Office Action Mailed Nov. 27, 2009", 13 pgs.

"U.S. Appl. No. 11/037,275, Notice of Allowance mailed Sep. 23, 2009", 6 pgs.

"U.S. Appl. No. 11/037,275, Response filed Aug. 13, 2009 to Final Office Action mailed Jun. 17, 2009", 14 pgs.

"U.S. Appl. No. 11/129,050, Advisory Action mailed Jul. 14, 2009", 3 pgs.

"U.S. Appl. No. 11/129,050, Notice of Allowance mailed Aug. 24, 2009", 7 pgs.

"U.S. Appl. No. 11/129,050, Notice of Allowance mailed Dec. 2, 2009", 4 pgs.

"U.S. Appl. No. 11/148,107, Notice of Allowance mailed Aug. 24, 2009", 4 pgs.

"U.S. Appl. No. 11/465,878, Notice of Allowance mailed Oct. 8, 2009", 8 pgs.

"U.S. Appl. No. 11/778,527, Non-Final Office Action mailed Aug. 24, 2009", 8 Pgs.

"U.S. Appl. No. 11/778,527, Response filed Nov. 24, 2009 to Non Final Office Action mailed Aug. 24, 2009", 11 pgs.

"European Application Serial No. 06762527.9, Communication pursuant to Rules 161 to 182 EPC mailed Mar. 3, 2008", 2 pgs.

"European Application Serial No. 06762527.9, Response filed Apr. 9, 2008 to Communication pursuant to Rules 161 to 182 EPC mailed Mar. 3, 2008", 6 pgs.

"International Application Serial No. PCT/US2006/018497, International Search Report mailed Oct. 24, 2006", 5 pgs.

"International Application Serial No. PCT/US2006/018497, Written Opinion mailed Oct. 24, 2006", 7 pgs.

"European Application Serial No. 07753005.3, Communication dated Nov. 5, 2008", 2 pgs.

"European Application Serial No. 07753005.3, Response filed Dec. 2, 2008 to Communication dated Nov. 5, 2008", 9 pgs.

"Japanese Application Serial No. 2009-502827, Amended Claims filed Mar. 4, 2010" (w/ English Translation), 15 pgs.

* cited by examiner

HEMODYNAMIC STABILITY ASSESSMENT BASED ON HEART SOUNDS

CROSS-REFERENCE TO RELATED APPLICATIONS

This application is related to the following co-pending, commonly assigned U.S. patent application Ser. No. 10/900,570 entitled "DETERMINING A PATIENT'S POSTURE FROM MECHANICAL VIBRATIONS OF THE HEART," filed on Jul. 28, 2004, Ser. No. 10/703,175, entitled "A DUAL USE SENSOR FOR RATE RESPONSIVE PACING AND HEART SOUND MONITORING," filed on Nov. 6, 2003, Ser. No. 10/334,694 entitled "METHOD AND APPARATUS FOR MONITORING OF DIASTOLIC HEMODYNAMICS," filed on Dec. 30, 2002, Ser. No. 10/746,874 entitled "A THIRD HEART SOUND ACTIVITY INDEX FOR HEART FAILURE MONITORING," filed on Dec. 24, 2003, Ser. No. 11/037,275, entitled "METHOD FOR CORRECTION OF POSTURE DEPENDENCE ON HEART SOUNDS," filed on Jan. 18, 2005, Ser. No. 11/129,050, entitled "METHOD AND APPARATUS FOR CARDIAC PROTECTION PACING," filed on May 16, 2005, and Ser. No. 11/148,107, entitled "ISCHEMIA DETECTION USING HEART SOUND SENSOR," filed on Jun. 8, 2005, each of which is hereby incorporated by reference.

TECHNICAL FIELD

The field generally relates to implantable medical devices and, in particular, but not by way of limitation, to systems and methods for monitoring mechanical activity of the heart.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Additionally, some IMDs detect events by monitoring electrical heart activity signals. In CFM devices, these events include heart chamber expansions or contractions. By monitoring cardiac signals indicative of expansions or contractions, IMDs are able to detect tachyarrhythmia. IMDs are further able to provide therapy for tachyarrhythmia, such as a high energy shock stimulus or anti-tachyarrhythmia pacing (ATP). Tachyarrhythmia includes abnormally rapid heart rate, or tachycardia, including ventricular tachycardia (VT) and supraventricular tachycardia. Tachyarrhythmia also includes rapid and irregular heart rate, or fibrillation, including ventricular fibrillation (VF). Typically, ICDs detect tachyarrhythmia by first detecting a rapid heart rate. Other detection methods in addition to fast rate detection are used to reduce the incidence of inappropriate shocks. The present inventors have recognized a need for improved sensing of events related to device treatment of tachyarrhythmia.

SUMMARY

This document discusses, among other things, systems and methods for monitoring mechanical activity of the heart. A system example includes an implantable medical device (IMD). The IMD includes an implantable sensor operable to produce an electrical signal representative of mechanical activity of a heart of a subject and a controller circuit coupled to the sensor. The IMD also includes a heart sound sensor interface circuit to produce a heart sound signal, a tachyarrhythmia detector, and a controller circuit. The controller circuit includes a hemodynamic stability assessment module configured to detect at least one episode of ventricular tachyarrhythmia in a subject and obtain a measurement of hemodynamic stability of the ventricular tachyarrhythmia from the heart sound signal.

A method example includes detecting at least one episode of ventricular tachyarrhythmia in a subject, sensing at least one heart sound signal for the subject using an IMD, and obtaining a measurement of hemodynamic stability of the ventricular tachyarrhythmia from the heart sound signal.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

This document discusses systems and methods for improved detection of cardiac events. A rapid and unstable heart rate associated with tachyarrhythmia can prevent the heart chambers from filling properly; resulting in a drop in a patient's blood pressure. Sometimes, a heart rate becomes rapid but a patient's hemodynamic system remains stable, i.e. the heart rate is regular enough so that the heart chambers are able to fill adequately to maintain adequate blood pressure. A proper assessment of hemodynamic system stability is important in making a decision in whether to deliver or to delay treatment, or whether to treat a tachyarrhythmia with either shock or ATP therapy. However, it is desirable that the decision be made in timely fashion.

Waiting too long to provide treatment may decrease the likelihood of successfully converting the rhythm once the chosen therapy is begun. Similarly, spending too much time trying various ATP regimens before resorting to shock therapy may also decrease the likelihood of successfully converting the tachyarrhythmia to a normal sinus rhythm. However, even a modest delay in providing treatment may allow an abnormal tachyarrhythmia rhythm to spontaneously revert back to normal. Delay of shock therapy may be warranted if it is known that the patient's blood pressure remains adequate. If a device is able to properly delay shock therapy, the number of inappropriate shocks is reduced, thereby enhancing patient comfort and extending the battery life of the device.

Blood pressure remains adequate during a stable tachyarrhythmia but becomes inadequately low during an unstable tachyarrhythmia. Making information related to a patient's blood pressure within the heart chambers available to a device improves the chances that the device will make a proper assessment of heart rhythm stability. A proper assessment makes it possible to delay the onset of treatment of a stable tachyarrhythmia or to extend the time to attempt to resolve the episode with ATP before resorting to high-energy shock therapy. This ensures that a high-energy shock stimulus will convert the abnormal rhythm if the rhythm fails to convert spontaneously or fails to convert after ATP.

Figure 1:
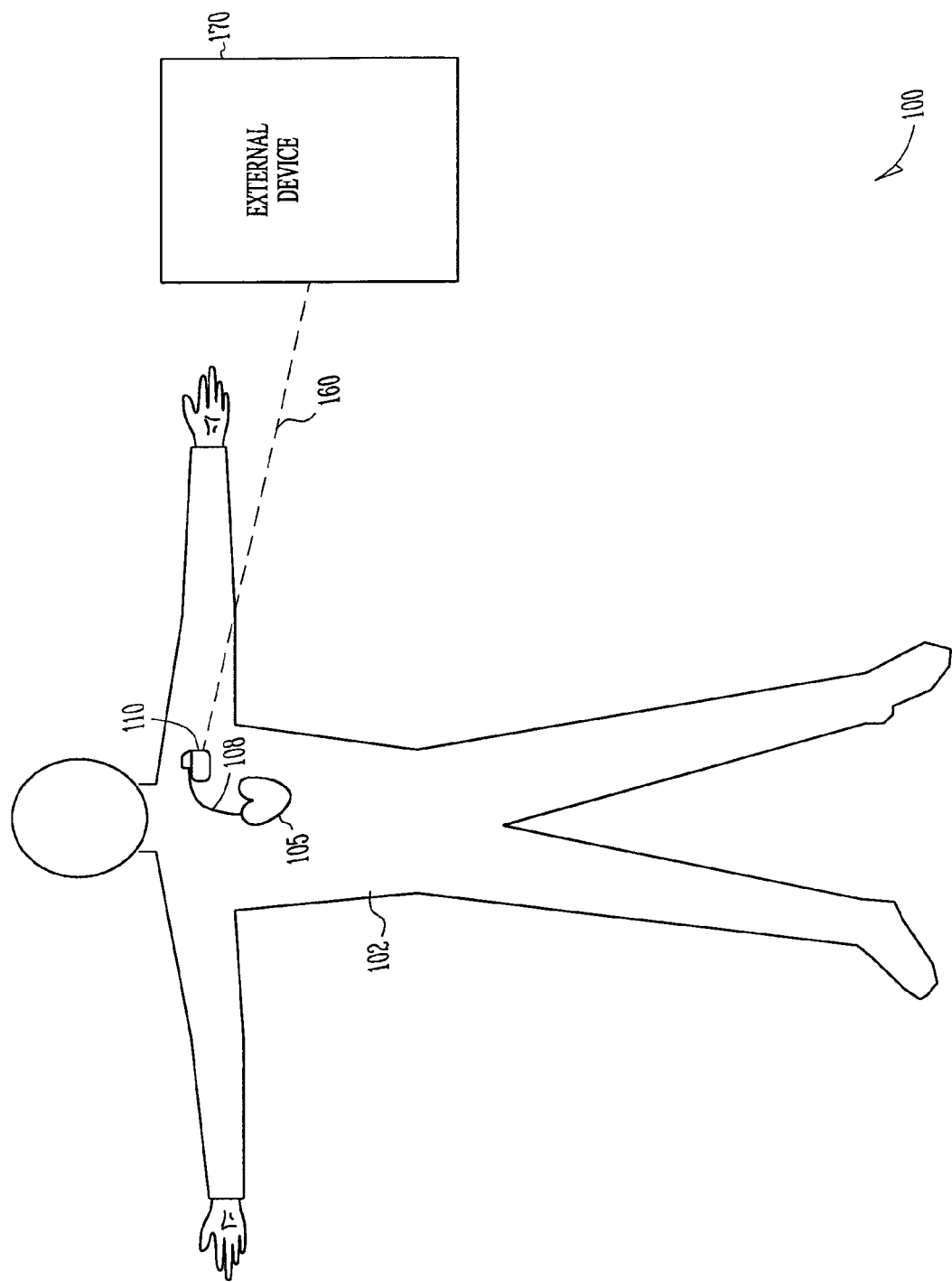
FIG. 1 is a block diagram of portions of a system that uses an implantable medical device (IMD).

FIG. 1 is a block diagram of portions of a system 100 that uses an implantable medical device (IMD) 110. As an example, the system 100 shown is used to treat a cardiac arrhythmia. The IMD 110 typically includes an electronics unit that is typically coupled by a cardiac lead 108, or additional leads, to a heart 105 of a patient 102, or otherwise associated with the heart 105. Examples of IMD 110 include, without limitation, a pacer, a defibrillator, a cardiac resynchronization therapy (CRT) device, or a combination of such devices. System 100 also typically includes an IMD programmer or other external device 170 that communicates wireless signals 160 with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electronics unit of the IMD 110 typically includes components that are enclosed in a hermetically-sealed canister or "can." Other electrodes may be located on the can, or on an insulating header extending from the can, or on other portions of IMD 110, such as for providing pacing energy, defibrillation energy, or both, in conjunction with the electrodes disposed on or around a heart 105. The lead 108 or leads and electrodes may also typically be used for sensing intrinsic or other electrical activity of the heart 105.

Figure 2A:
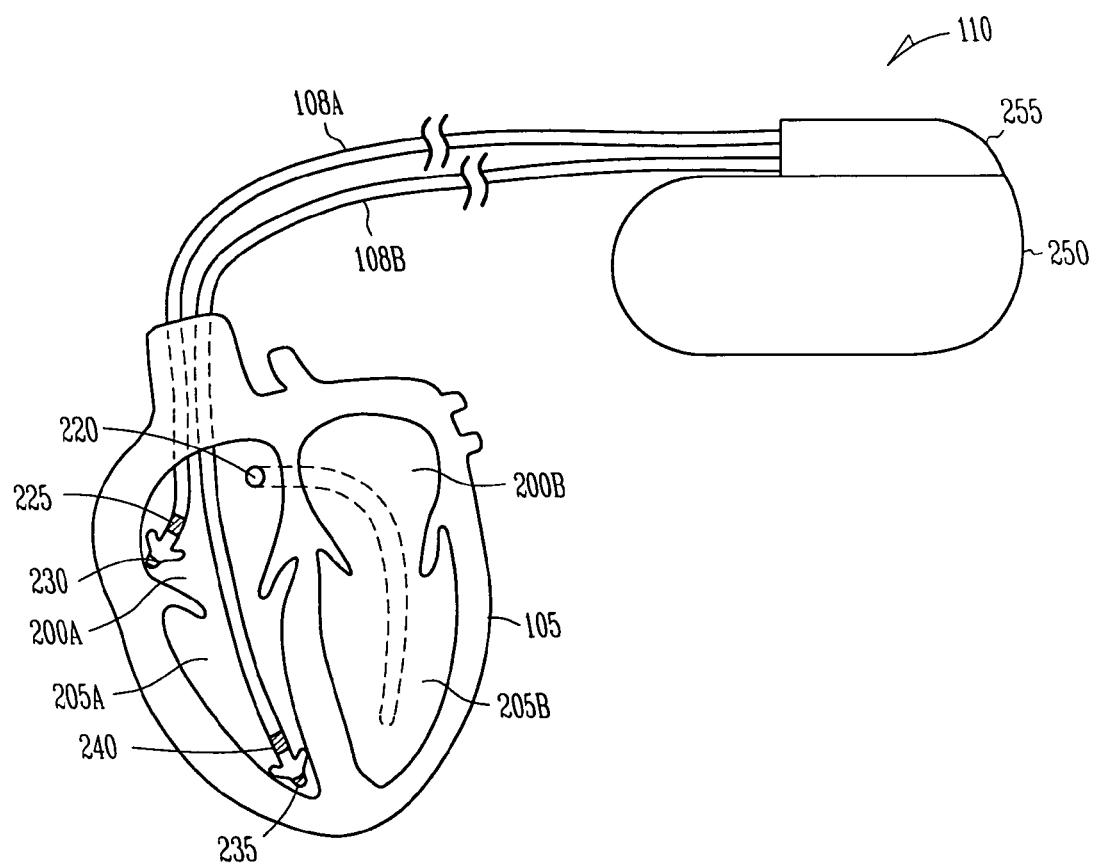
FIGS. 2A-B illustrate IMDs coupled by one or more leads to heart.
Figure 2B:
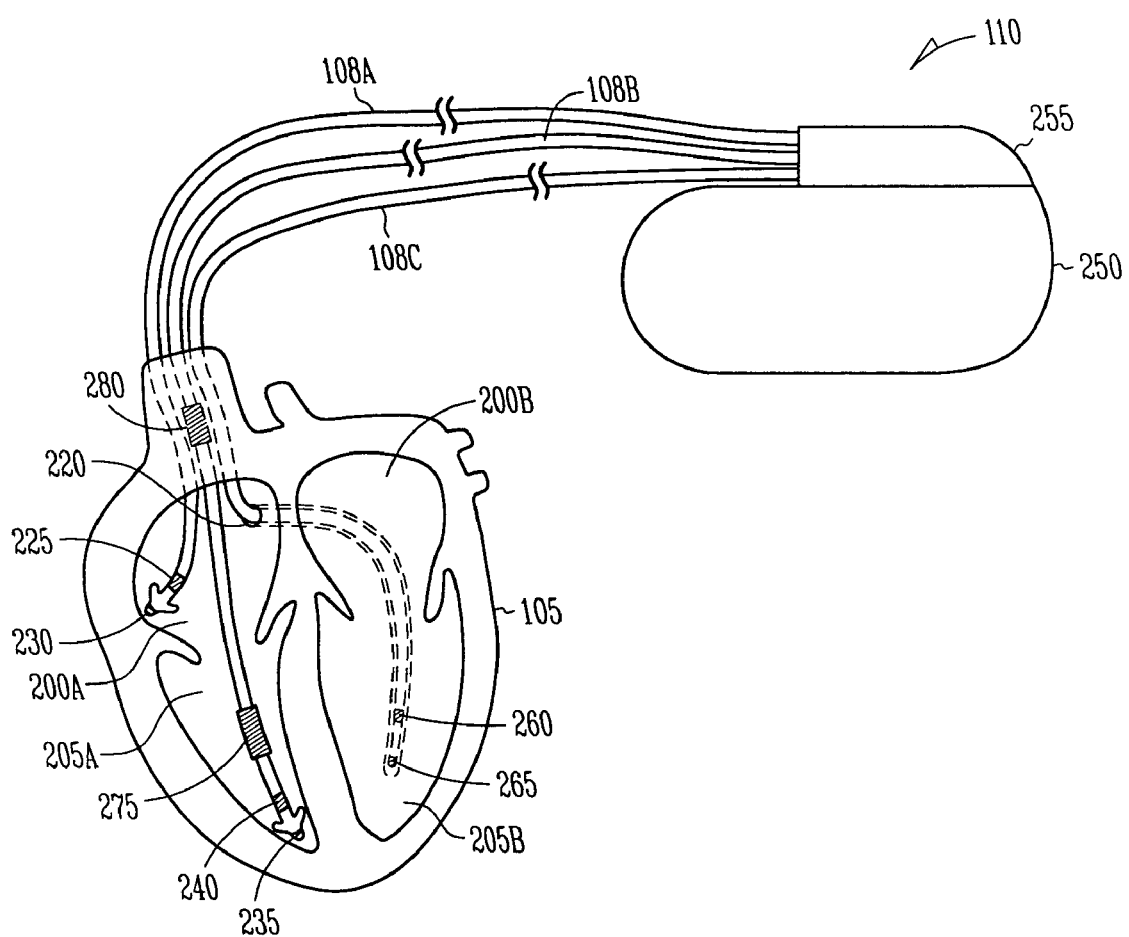

FIGS. 2A-B illustrate IMDs 110 coupled by one or more leads 108A-C to heart 105. Heart 105 includes a right atrium 200A, a left atrium 200B, a right ventricle 205A, a left ventricle 205B, and a coronary sinus 220 extending from right atrium 200A. In the example in FIG. 2A, atrial lead 108A includes electrodes (electrical contacts, such as ring electrode 225 and tip electrode 230) disposed in an atrium 200A of heart 105 for sensing signals, or delivering pacing therapy, or both, to the atrium 200A.

Ventricular lead 108B includes one or more electrodes, such as tip electrode 235 and ring electrode 240, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such defibrillation electrodes typically have larger surface areas than pacing electrodes in order to handle the larger energies involved in defibrillation. Lead 108B optionally provides resynchronization therapy to the heart 105.

In some examples, leads 108A and 108B are combined into one lead containing four electrodes located sequentially along the lead. In an example, a first tip electrode is located in the apex of the right ventricle 205A, a first ring electrode located proximal to the tip electrode and in the right ventricle 205A, a second ring electrode located proximal to the first ring electrode and in the right atrium 200A, and a third ring electrode located proximal to the second ring electrode and also located in the right atrium 200A.

The example in FIG. 2B includes a third cardiac lead 108C attached to the IMD 110 through the header 255. The third lead 108C includes ring electrodes 260 and 265 placed in a coronary vein lying epicardially on the left ventricle (LV) 205B via the coronary vein 220. In the example, lead 108B further includes a first defibrillation coil electrode 275 located proximal to tip and ring electrodes 235, 240 for placement in a right ventricle (RV), and a second defibrillation coil electrode 280 for placement in the superior vena cava (SVC) located proximal to the first defibrillation coil 275, tip electrode 235, and ring electrode 240. In some examples, high energy shock therapy is delivered from the first or RV coil 275 to the second or SVC coil 280. In some examples, the SVC coil 280 is electrically tied to an electrode formed on the IMD can 250. This improves defibrillation by delivering current from the RV coil 275 more uniformly over the ventricular myocardium. In some examples, the therapy is delivered from the RV coil 275 only to the electrode formed on the IMD can 250.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrodes.

Figure 3A:
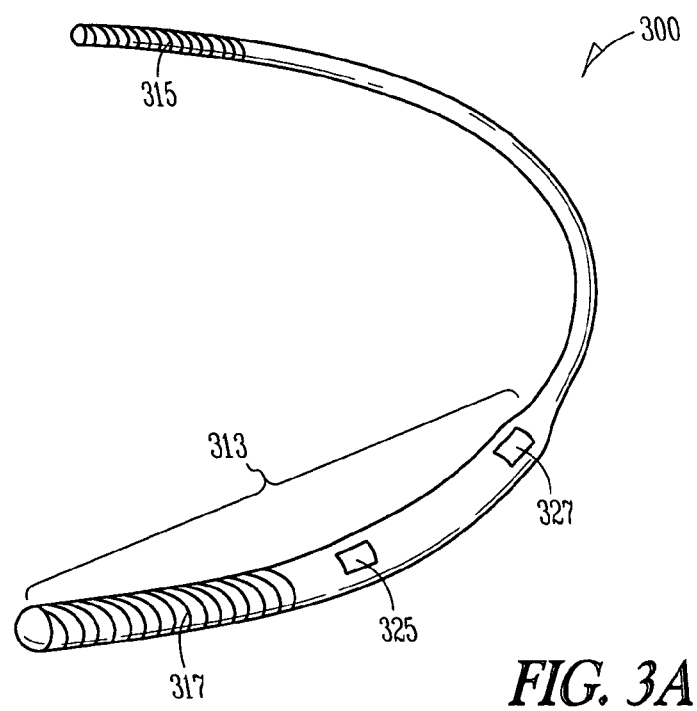
FIGS. 3A-B show an example of an IMD that does not use intravascular leads to sense cardiac signals.
Figure 3B:
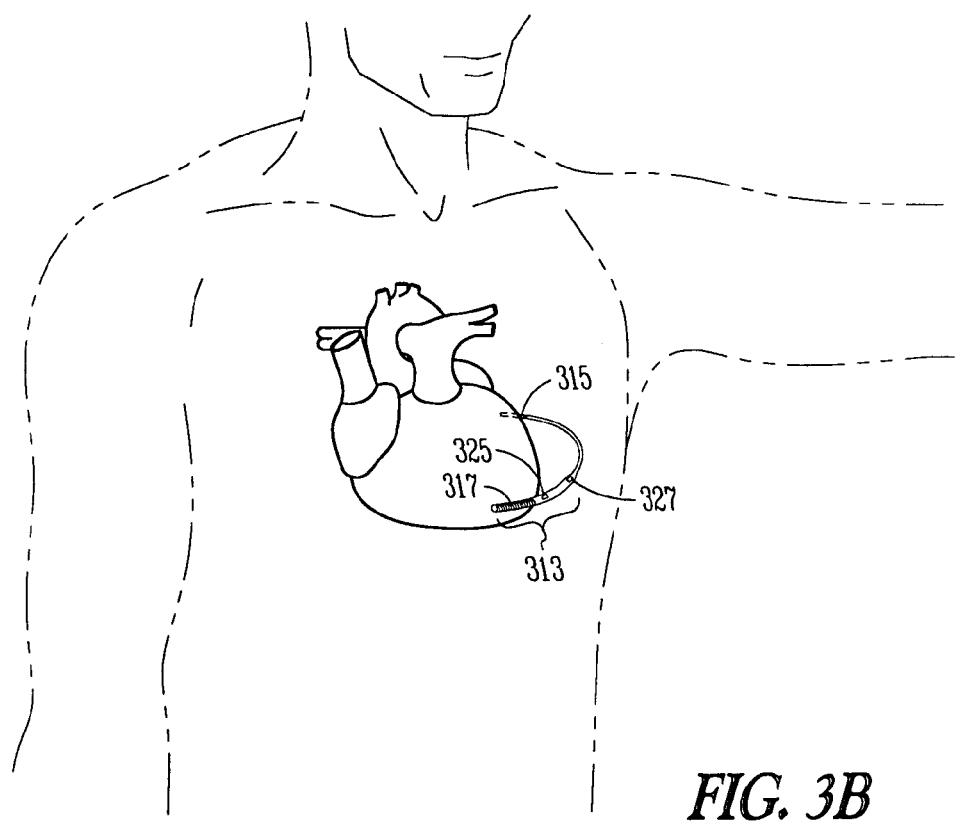

FIGS. 3A-B show an example of an IMD 300 that does not use intravascular leads to sense cardiac signals. FIG. 3A shows that the IMD 300 includes a thicker end 313 to hold the power source and circuits. The IMD 300 also includes electrodes 325 and 327 for remote sensing of cardiac signals. Cardioversion/defibrillation is provided through electrodes 315 and 317. FIG. 3B shows an example of the position of the IMD 300 within a patient.

IMDs can include sensors to monitor heart sounds. An accelerometer is one type of heart sound sensor. An accelerometer converts an acceleration signal due to acoustic vibrations of a heart sound into an electrical signal. A microphone is another type of heart sound sensor. A strain gauge is yet another type of heart sound sensor. A strain gauge converts deformation of the sensor due to heart sound vibrations into an electrical signal. Heart sounds include the "first heart sound" or S1, the "second heart sound" or S2, the "third heart sound" or S3, the "fourth heart sound" or S4, and their various sub-components. S1 is indicative of, among other things, mitral valve closure, tricuspid valve closure, and aortic valve opening. S2 is indicative of, among other things, aortic valve closure and pulmonary valve closure. S3 is a ventricular diastolic filling sound often indicative of certain pathological conditions including heart failure. S4 is a ventricular diastolic filling sound resulted from atrial contraction and is usually indicative of pathological conditions. The term "heart sound" refers to any heart sound (e.g., S1) and any components thereof (e.g., M1 component of S1, indicative of mitral valve closure). The term heart sound also includes audible and inaudible mechanical vibrations caused by cardiac activity that can be sensed with an accelerometer.

Monitoring heart sounds allows measurement of hemodynamic performance parameters. Heart sounds signals obtained from heart sound sensors are indicative of timing, strength, and frequency characteristics related to the heart sounds. Measuring these characteristics allows conclusions to be made about the condition of a patient's hemodynamic system.

Figure 4:
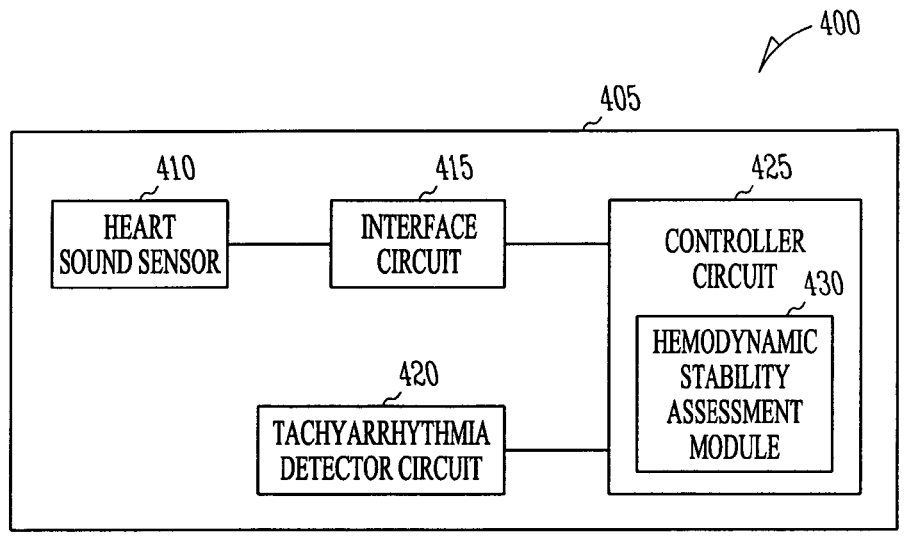
FIG. 4 is a block diagram illustrating portions of an IMD used to obtain patient hemodynamic information from heart sounds.

FIG. 4 is a block diagram 400 illustrating portions of an IMD 405 used to obtain patient hemodynamic information from heart sounds. The IMD 405 includes a an implantable heart sound sensor 410, a heart sound sensor interface circuit 415, a tachyarrhythmia detector circuit 420, and a controller circuit 425 that, in turn, includes a hemodynamic stability assessment module 430. The implantable heart sound produces an electrical signal representative of at least one heart sound. The heart sound associated with mechanical activity of a patient's heart. In some embodiments, the implantable heart sound sensor 410 includes an accelerometer. In some embodiments, the heart sound sensor 410 includes a strain gauge. In some embodiments, the heart sound sensor 410 includes a microphone.

Figure 5:
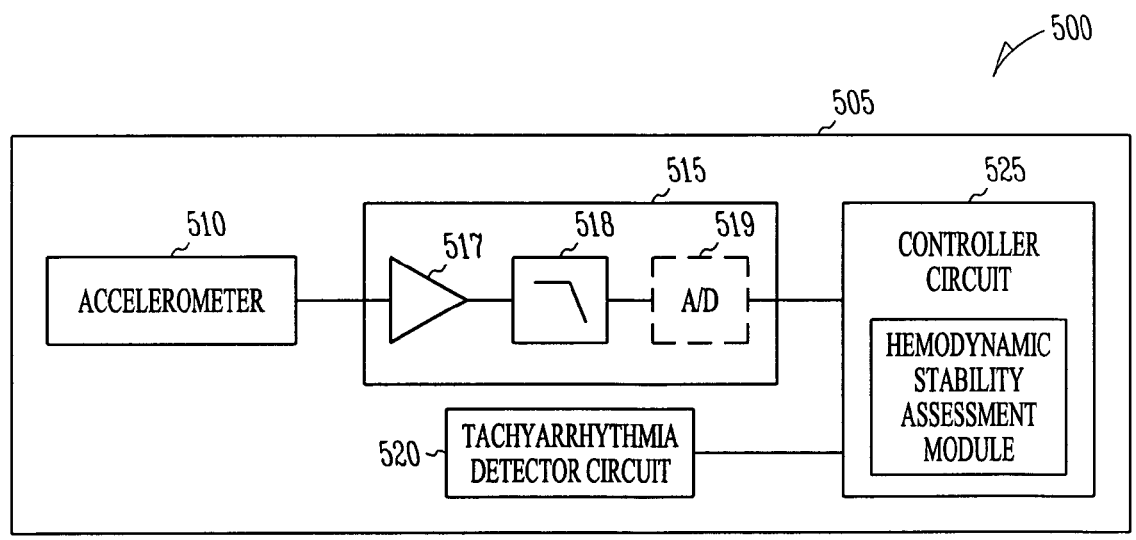
FIG. 5 shows a block diagram of portions of another example of an IMD.

The heart sound sensor interface circuit 415 produces a heart sound signal. FIG. 5 shows a block diagram 500 of portions of an example of an IMD 505 where the heart sound sensor is an accelerometer 510 and the heart sound sensor interface circuit 515 includes an amplifier circuit 517 and a filter circuit 518. In some examples, the amplifier circuit 517 is a voltage amplifier that has a signal gain of about one thousand and the filter circuit 518 is a low-pass filter circuit having single pole roll-off with a corner frequency between fifty hertz (50 Hz) to eighty hertz (80 Hz). In some examples, the controller circuit 525 adjusts the parameters of the amplifier circuit 517 and filter circuit 518. As illustrative examples, the controller circuit is configured to adjust the gain of the amplifier circuit 517 and to adjust the corner frequency of the filter circuit 518 or to change the filter circuit 518 from single to double pole roll-off. In some examples, the heart sound sensor interface circuit 515 includes an analog-to-digital (A/D) converter circuit 519 to convert the analog heart sound signal from accelerometer 510 into digital values.

The energy content in heart sounds is predominantly contained in lower frequencies. In some examples, if the low-pass filter circuit 518 has a sharp roll-off, the heart sound sensor interface circuit 515 includes a pre-emphasis circuit. The pre-emphasis circuit has a transfer function of a high-pass filter circuit, but with a lower order than the low-pass filter circuit. The pre-emphasis circuit adds signal gain to higher frequencies of a low-pass filtered heart sound signal. These frequencies include those near the corner frequency of the low-pass filter for example. If the heart sound signal has been digitized, the pre-emphasis transfer function can be implemented mathematically by the controller circuit 525. The term "controller circuit" includes a microcontroller, a microprocessor, a digital signal processor, or application specific integrated circuit (ASIC).

Returning to FIG. 4, the controller circuit 425 is configured to execute a function or functions. Such functions correspond to modules, which are software, hardware, firmware or any combination thereof. Multiple functions are performed in one or more modules. The controller circuit 425 includes a hemodynamic stability assessment module 430. The hemodynamic stability assessment module 430 can be configured to receive information indicating that at least one episode of ventricular tachyarrhythmia in a subject has been detected by the tachyarrhythmia detector circuit 420, and to obtain a measurement of hemodynamic stability of the ventricular tachyarrhythmia from the heart sound signal.

In an illustrative example, the tachyarrhythmia detector circuit 420 is coupled to a ventricular contraction sensing circuit and ventricular tachyarrhythmia is detected from a rapid ventricular contraction rate. If the measurement of hemodynamic stability indicates that the tachyarrhythmia is hemodynamically stable, treatment for the tachyarrhythmia can be delayed, or the time to attempt to resolve the episode with ATP can be extended, before resorting to high-energy shock therapy.

Figure 6:
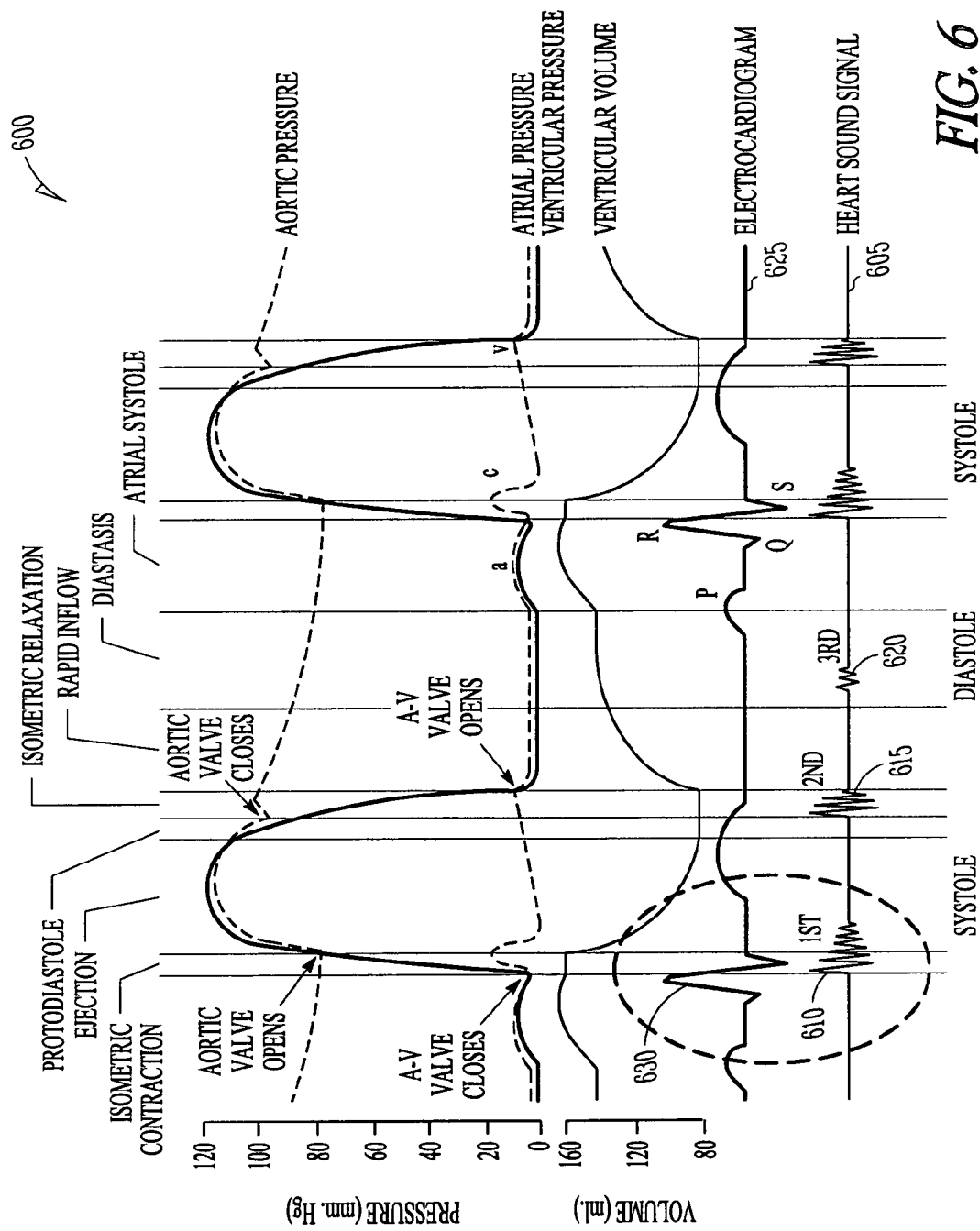
FIG. 6 shows waveforms corresponding to cardiac cycles.

FIG. 6 shows waveforms 600 corresponding to sensed cardiac cycles. The heart sound signal waveform 605 shows the relationship of the first, second, and third heart sounds (610, 615, 620) to the P-wave and the QRS cardiac complex of an electrocardiogram 625. Because heart sounds are associated with mechanical function of the heart, a measurement of a hemodynamic parameter based on heart sounds can be a proxy measurement of hemodynamic stability based on aortic pressure.

One method to obtain a measurement of hemodynamic stability is to use linear prediction. Linear prediction is a statistical analysis tool that can be used to estimate future values of a sampled or discrete time function based on previous sampled values. In some examples, the measurement of hemodynamic stability is a heart sound based hemodynamic parameter He which is defined as $$He = 1 - k_1^2, \qquad (1)$$

where $k_1$ is a first reflection parameter. The first reflection parameter $k_1$ is a function of the first and second autocorrelation terms $R_0$ and $R_1$. Specifically, $$k_1 = -\left(\frac{R_1}{R_0}\right). \qquad (2)$$

If a set of N digitized samples $(s_0, s_1, s_2, s_3 \ldots)$ is taken over one measured heart sound, then the first and second autocorrelation terms $R_0$ and $R_1$ can be calculated as $$R_0 = \sum_{n=0}^{N-1} s_n^2, \text{ and} \qquad (3)$$

-continued $$R_1 = \sum_{n=0}^{N-2} s_n s_{n+1}. \qquad (4)$$

Figure 7:
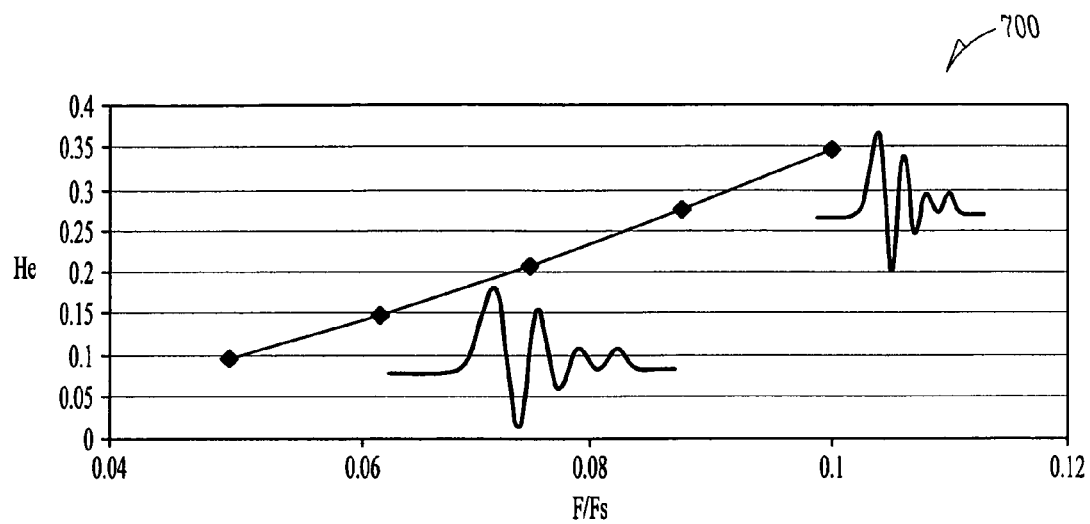
FIG. 7 shows a graph of a measurement of hemodynamic stability.

In some examples, the hemodynamic parameter He is based on the S1 heart sound. FIG. 7 shows a graph 700 of He obtained from the S1 heart sound as a function of the ratio of the frequency of the measured S1 heart sound to the sampling frequency. The graph 700 shows that He will vary with frequency of the heart sound, which a measured with a fixed sampling rate.

Figure 8:
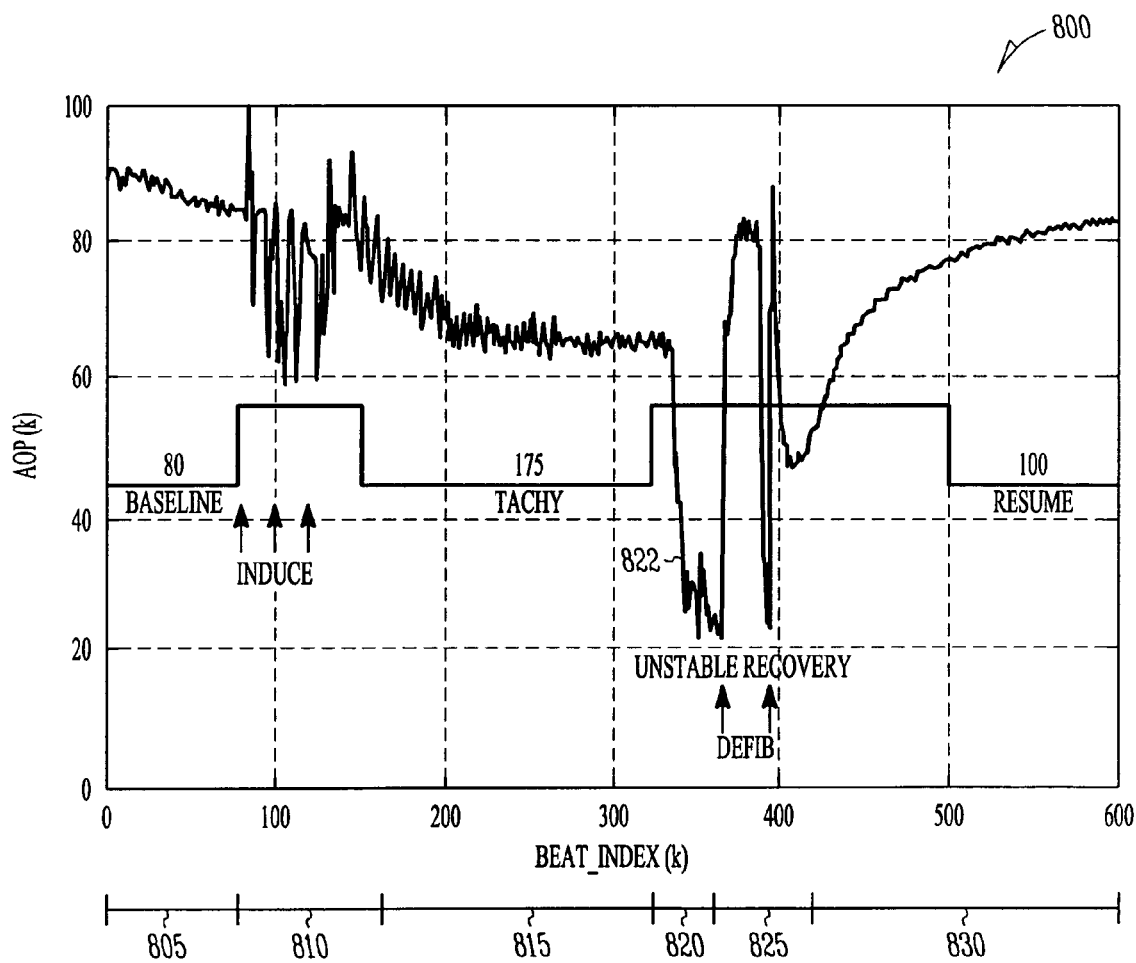
FIG. 8 is a graph of aortic pressure as a function of heart beats of a subject.

FIG. 8 is a graph 800 of aortic pressure as a function of heart beats of a subject. In the first region 805, a baseline of He can be established. In the second region 810, an episode of tachyarrhythmia was induced in the subject. The third region 815 shows the change in aortic pressure during the episode of tachyarrhythmia. After more than one hundred beats in stable tachyarrhythmia in region 815, the episode became unstable in region 820 and a large corresponding decrease in aortic pressure 822 is evident. The graph 800 shows defibrillation in region 825 followed by recovery in region 830.

Figure 9:
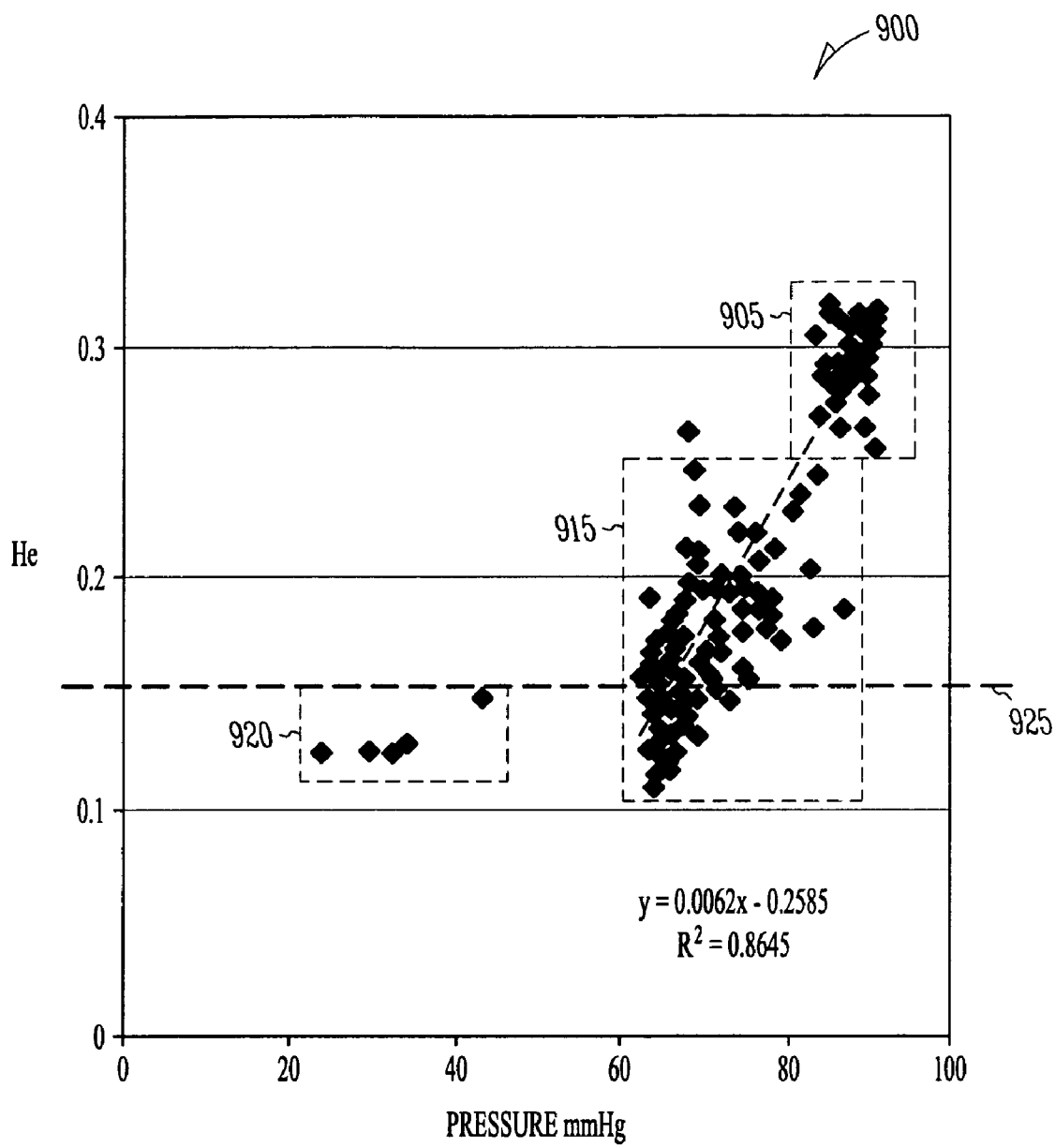
FIG. 9 shows a graph of a measurement of hemodynamic stability versus aortic pressure.

The hemodynamic parameter He was measured on a beat-by-beat basis for the S1 heart sound during the episode. FIG. 9 shows a graph 900 of the measured He versus aortic pressure. Region 905 shows a concentration of measured He corresponding to the baseline 815 in FIG. 8. Region 915 shows a concentration of measured He corresponding to the stable tachyarrhythmia of region 815 in FIG. 8. The graph 900 shows a decrease in both the measured He and the aortic pressure between regions 905 and 915. FIG. 7 shows that the hemodynamic parameter He decreases if the frequency components of the heart sound decrease. The decrease in the frequency components of the S1 heart sound (evidenced by the decrease in the hemodynamic parameter He) that occur with the decrease in aortic pressure may be due to the change in contractility of the heart during tachyarrhythmia. Region 920 shows a concentration of measured He corresponding to the unstable tachyarrhythmia of region 820. Note that while the graph 900 shows an overlap with some measured values of He, there is a large decrease in aortic pressure indicating that the tachyarrhythmia became unstable.

The graph 900 also shows that a threshold value T 925 of measured He can be chosen so that if, during tachyarrhythmia, a value of He less than the threshold value 925 is measured, the patient's aortic blood pressure may have become inadequately low. The tachyarrhythmia is deemed to be unstable due to the possibly low blood pressure and shock therapy should be administered to the patient. If during tachyarrhythmia, a value higher than the threshold value 925 is measured, treatment can be delayed or a regimen of ATP can be administered to the patient instead of, or prior to, delivery of a shock. In another example, the tachyarrhythmia is deemed to be unstable if a value of He less than the threshold value 925 is measured in X of Y consecutive cardiac cycles, where X and Y are integers and Y≧X. In one example, an appropriate threshold value 925 of measured He can be determined from a database containing sampled heart sound data and pressure data from several tachyarrhythmia patients. In another example, an appropriate threshold value 925 of measured He specific to one patient can be determined from a database containing such data only for that patient.

The graph 900 also shows that a baseline value of measured He can be determined for a patient when the patient is not experiencing tachyarrhythmia (region 905). In an example, the baseline is determined from a central tendency of the measured He, such as mean value or a median value. A patient's aortic blood pressure may have become inadequately low if the measured He changes from the baseline He value by more than a predetermined threshold value. A corresponding detected tachyarrhythmia is then deemed to be unstable. In another example, the tachyarrhythmia is deemed to be unstable if the measured He changes, such as a decrease, from the baseline He value by more than a predetermined threshold value in X of Y consecutive cardiac cycles, where X and Y are integers and Y≧X.

Returning to FIG. 4 and in light of the previous discussion, in some examples, the heart sound sensor interface circuit 415 includes a sampling circuit to obtain a sampled heart sound signal and the hemodynamic stability assessment module 430 includes an autocorrelation module to obtain the measurement of hemodynamic stability He by determining an autocorrelation function using the sampled heart sound signal. The hemodynamic stability assessment module 430 deems the ventricular tachyarrhythmia to be unstable when the measurement of hemodynamic stability He is below a predetermined threshold value, such as a fixed or programmable threshold value.

In some examples, the hemodynamic stability assessment module 430 includes a baseline module to establish a baseline for the measurement of hemodynamic stability obtained from the heart sound signal. The hemodynamic stability assessment module 430 deems the ventricular tachyarrhythmia to be unstable, such as when a measured change from the baseline measurement of hemodynamic stability exceeds a predetermined threshold value.

Figure 10:
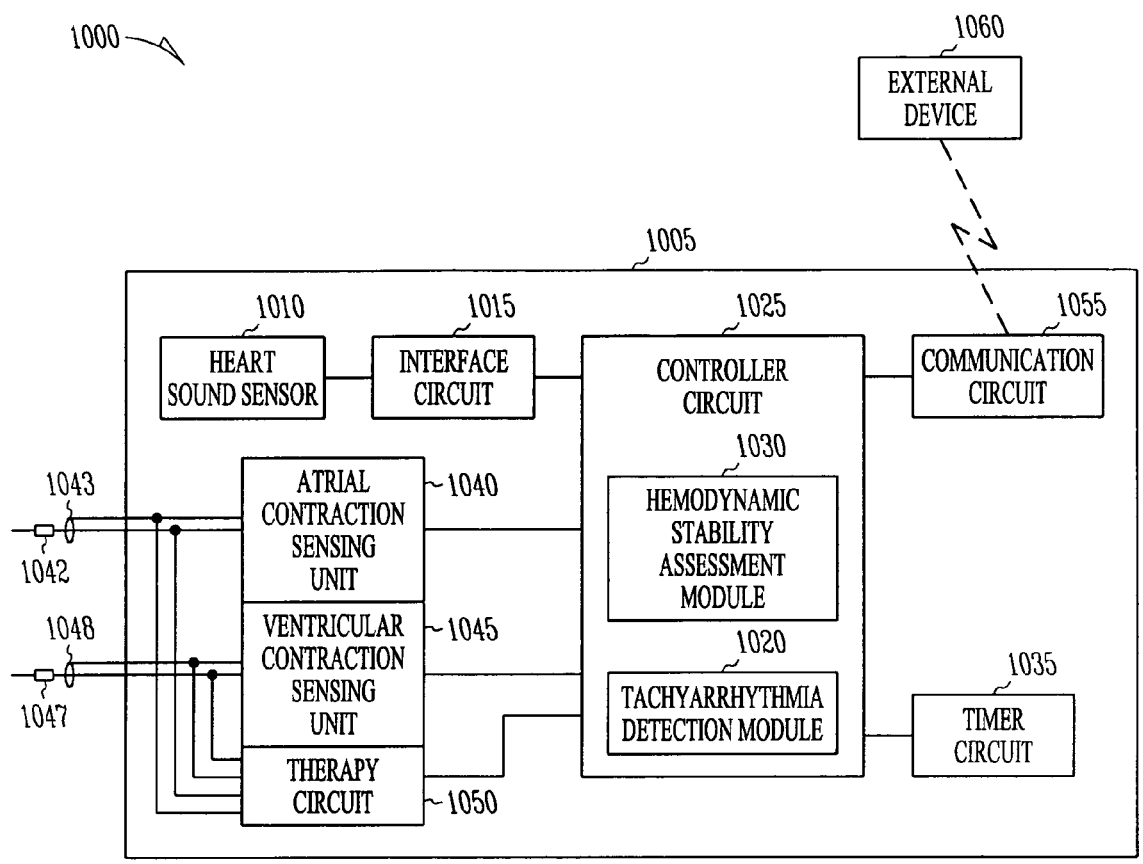
FIG. 10 is a block diagram illustrating portions of a system that includes an IMD used to obtain patient hemodynamic information from heart sounds.

FIG. 10 is a block diagram 1000 illustrating portions of a system that includes an IMD 1005 used to obtain patient hemodynamic information from heart sounds. The IMD 1005 includes an implantable heart sound sensor 1010, a heart sound sensor interface circuit 1015, and a controller circuit 1025 that, in turn, includes a hemodynamic stability assessment module 1030.

The IMD 1005 also includes a tachyarrhythmia detector circuit comprising a tachyarrhythmia detection module 1020, a timer circuit 1035, and a ventricular contraction sensing circuit 1045. In some examples, the tachyarrhythmia detector circuit also includes an atrial contraction sensing circuit 1040. The atrial contraction sensing circuit 1040 provides a sensed atrial contraction signal. In the example shown, the atrial signal is sensed between lead tip electrode 1042 and lead ring electrode 1043. The ventricular contraction sensing circuit 1045 provides a sensed ventricular contraction signal. In the example shown, the ventricular signal is sensed between lead tip electrode 1047 and lead ring electrode 1048.

In some examples, the tachyarrhythmia detection module 1020 declares that a ventricular tachyarrhythmia has occurred based on the ventricular contraction rate. For example, the tachyarrhythmia detection module 1020 typically declares that a ventricular tachyarrhythmia has occurred when the ventricular contraction rate exceeds a threshold ventricular contraction rate. In some examples, the tachyarrhythmia detection module 1020 performs a rhythm discrimination method that includes recurrently updating an average ventricular contraction interval (V-V interval). In certain examples, the tachyarrhythmia detection module 1020 declares that a ventricular tachyarrhythmia has occurred when determining that an average ventricular contraction rate exceeds an average atrial contraction rate by more than a specified rate threshold value. In some examples, the tachyarrhythmia detection module 1020 declares that a ventricular tachyarrhythmia has occurred based on a measure of variability of the ventricular contraction intervals.

If at least one episode of ventricular tachyarrhythmia in a subject is detected, the hemodynamic stability assessment module 1030 determines a measurement of hemodynamic stability of the ventricular tachyarrhythmia, such as from a heart sound signal. In some examples, the hemodynamic stability assessment module 1030 deems that a tachyarrhythmia is unstable based on: (1) a measurement of hemodynamic stability and (2) on an indication of unstable tachyarrhythmia received from the tachyarrhythmia detection module 1020. In some examples, such an indication of unstable tachyarrhythmia includes a measure of variability of the ventricular contraction intervals exceeding a predetermined variability threshold.

In an example, the hemodynamic stability module 1030 includes a baseline module to establish a baseline for the measurement of hemodynamic stability obtained from a heart sound signal. In an illustrative example, the measurement is the hemodynamic parameter He obtained from the S1 heart sound signal. In this example, the hemodynamic stability assessment module 1030 deems the ventricular tachyarrhythmia to be unstable when both a measured change from the baseline measurement of hemodynamic stability exceeds a predetermined stability measurement threshold value and the measure of variability of ventricular time intervals exceeds a predetermined variability threshold value.

The IMD 1005 also typically includes a therapy circuit 1050. The therapy circuit 1050 typically includes a shock circuit to provide a high energy shock as a therapy for tachyarrhythmia. In some examples, the therapy circuit includes a switch network to electrically isolate sense amplifiers in the sensing circuits 1040, 1045 during delivery of the shock in order to prevent damage to the sense amplifiers. The controller circuit 1025 can be configured to delay delivery of a predetermined shock if the hemodynamic stability assessment module indicates the tachyarrhythmia is stable. In some examples, the measurement of hemodynamic stability is the hemodynamic parameter He and the controller circuit 1025 delays delivery of a shock if the measured He is below a predetermined threshold He value. In some examples, the controller circuit 1025 delays delivery of a shock stimulus if the measured He is different from a baseline He value by less than a predetermined threshold value.

In some examples, the therapy circuit 1050 includes an anti-tachyarrhythmia pacing (ATP) circuit coupled to the controller circuit. The controller circuit 1025 initiates a predetermined ATP regimen upon detecting the episode of ventricular tachyarrhythmia and extends the duration of the ATP regimen according to the measurement of hemodynamic stability. In some examples, the measurement of hemodynamic stability is the hemodynamic parameter He and the controller circuit 1025 extends the duration of the ATP regimen if the measured He is below a predetermined threshold He value. In some examples, the controller circuit 1025 extends the duration of the ATP regimen if the measured He is different from a baseline He value by less than a predetermined threshold value.

In some examples, the ventricular contraction sensing circuit 1045 produces an electrical cardiac signal representative of cardiac activity of the patient. This cardiac signal is similar to the electrocardiogram signal 625 in FIG. 6. In some examples, the IMD 1005 includes an A/D circuit to obtain digitized samples of the cardiac signal. The cardiac signal is useful in identifying the different heart sounds. In some examples, the controller circuit 1005 tracks maximum values of the digitized samples of the cardiac signal to identify a QRS complex 630 as shown in FIG. 6. The QRS complex 630 can be used to identify the S1 heart sound 610. The controller circuit 1025 in FIG. 10 then initiates obtaining digitized samples of the heart sound signal provided by the heart sound interface circuit 1015 in correlation to the occurrence of the QRS complex. The digitized samples are obtained during a window of predetermined time duration. A measurement of hemodynamic stability is then obtained from the digitized samples by the hemodynamic stability assessment module 1030.

Sensors can be included in cardiac function management (CFM) devices, such as to monitor a patient's activity. Indications of a patient's activity level are sometimes used to adjust a rate of pacing therapy of a CFM device. Generally, these CFM devices increase a pacing rate in response to an increased activity level of the patient indicated by the sensor. This is sometimes referred to as rate responsive pacing. An accelerometer is one type of sensor that provides electrical signals representative of patient activity. It is sometimes preferable to monitor heart sound signals while a patient is at rest. Thus, in some examples, the hemodynamic stability assessment module 1030 is configured to obtain the measurement of hemodynamic stability from a heart sound signal in correlation with patient activity. Determining that a patient is at rest can be deduced from a patient's heart rate if the IMD 1005 includes rate responsive pacing therapy—i.e. the patient's heart rate is at the resting heart rate when the patient is at rest.

In some examples, the IMD 1005 includes a communication circuit 1055 and the controller circuit 1025 wirelessly communicates to the external device 1060 information about at least one measurement of hemodynamic stability obtained from a heart sound signal. In some examples, the external device 1060 is an IMD programmer. In some examples, the external device 1060 is part of, or is in communication with, a computer network such as a hospital computer network or the internet. In some examples, the external device 1060 is in communication with a mobile telephone network. In some examples, the external device is a repeater that communicates wirelessly with the IMD 1005 and with a third device in communication with a network, such as a computer network or mobile telephone network. In some examples, the third device is an IMD programmer.

The controller circuit 1025 communicates an indication of a detected tachyarrhythmia to the external device 1060. The indication can include information that the tachyarrhythmia is stable or unstable. The indication can be an entire digitized representation of a heart sound, a digitized representation of a cardiac signal, or an entire digitized representation of both a heart sound and a cardiac signal. The digitized representation can be displayed on the external device 1060 or another device connected to the network.

In some examples, the indication triggers an alarm on the external device 1060. In some examples, an indication of an unstable tachyarrhythmia triggers the alarm. In some examples, the alarm includes a notification sent to a clinician or clinician's office over the computer network, such as by e-mail, or the alarm includes an indication on a web page. In some examples, the alarm includes an indication or notification sent to a medical device service center or an emergency responder. In some examples, the IMD 1005 includes a speaker and the indication of tachyarrhythmia is an audible alarm originating from the IMD 1005.

Figure 11:
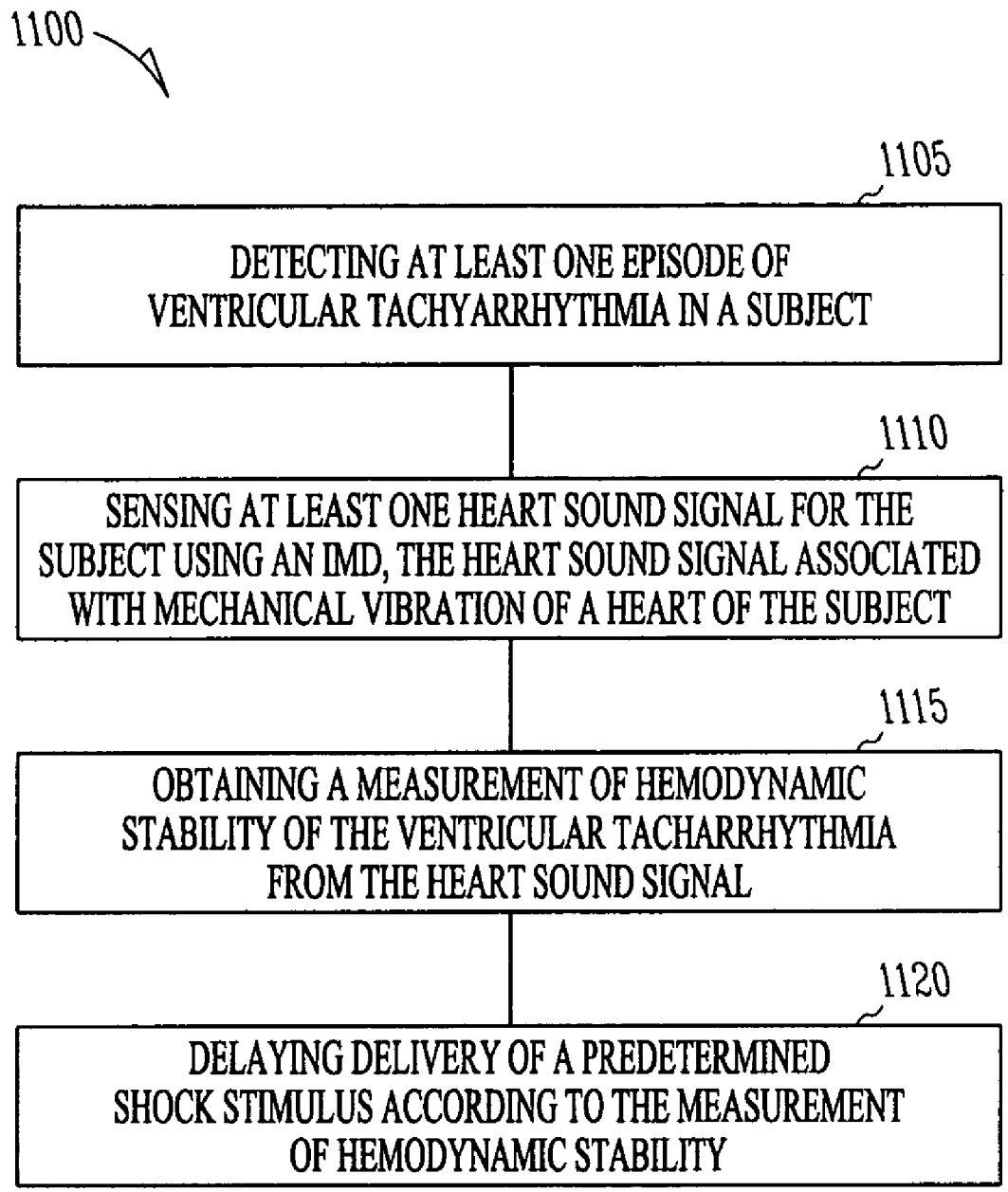
FIG. 11 is a block diagram of a method of monitoring mechanical activity of a heart.

FIG. 11 is a block diagram of a method 1100 of monitoring mechanical activity of a heart. At 1105, at least one episode of ventricular tachyarrhythmia is detected in a subject. In some examples, an episode of ventricular tachyarrhythmia is detected based on the ventricular contraction rate. In some examples, an episode of ventricular tachyarrhythmia is detected when it is determined that an average ventricular contraction rate exceeds an average atrial contraction rate by more than a specified rate threshold value. In some examples, an episode of ventricular tachyarrhythmia is detected based on a measure of variability of the ventricular contraction intervals.

At 1110, at least one heart sound signal for the subject is sensed using an IMD. The heart sound signal is associated with mechanical vibration of a heart of the subject. In some examples, the heart sound is the S1 heart sound. In some examples, the heart sound signal is sensed with an accelerometer and the heart sound signal is low-pass filtered to obtain a filtered heart sound signal. In some examples, higher frequencies of the filtered heart sound signal are pre-emphasized to add signal gain to the higher frequency signal components.

In some examples, sensing a heart sound signal with an IMD includes sensing an electrical cardiac signal that is representative of cardiac activity of the patient. Heart sounds are identified, such as by correlating the sensed heart sound signal to the sensed electrical cardiac signal. For example, as shown in FIG. 6, if the electrical cardiac signal and the heart sound signal are correlated in time, then identifying a QRS complex in the sensed electrical cardiac signal 625 helps identify the S1 heart sound 610. In some examples, digitized samples of the heart sound signal are obtained in correlation to the occurrence of a feature of the electrical cardiac signal, such as the QRS complex. In some examples, the digitized samples are obtained during a window of predetermined time duration. The window is defined relative to an occurrence of a feature of the electrical cardiac signal.

Returning to FIG. 11, at 1115 a measurement of hemodynamic stability of the ventricular tachyarrhythmia from the heart sound signal is obtained. In some examples, obtaining a measurement of hemodynamic stability includes extracting a proxy measurement of aortic pressure from the heart sound signal. In some examples, the heart sound signal includes the S1 heart sound. In some examples, the heart sound signal includes other heart sounds.

In some examples, obtaining a measurement of hemodynamic stability includes sampling the heart sound signal to obtain a plurality of signal samples. In some examples, the signal samples are used to determine an autocorrelation function. In some examples, the measurement of hemodynamic stability is the hemodynamic parameter He which is calculated by any of the methods of calculating He discussed previously.

In some examples, a measurement of hemodynamic stability from the heart sound signal includes establishing a baseline measurement for the measurement of hemodynamic stability. In some examples, establishing a baseline measurement includes determining a central tendency of the measurement of hemodynamic stability. In some examples, the method 1100 includes deeming the ventricular tachyarrhythmia to be unstable when a measured change from the baseline measurement of hemodynamic stability exceeds a predetermined threshold value. In some examples, the method 1100 includes deeming the ventricular tachyarrhythmia to be unstable when a measured change from the baseline measurement of hemodynamic stability exceeds a predetermined threshold value in X of Y consecutive cardiac cycles, wherein X and Y are integers and $Y \geq X$.

It is sometimes preferable to monitor heart sounds while a patient is at rest. In some examples, sensing a heart sound signal with an IMD includes sensing the signal in correlation to sensed patient activity to provide an indication of when the patient is at rest. Information that a patient is or is not at rest can be used in the determination of stable or unstable tachyarrhythmia. For example, knowing a rest state of a patient may be used to decide whether to use X of Y consecutive cardiac cycles, or used to set the values of X and Y.

In some examples, the method 1100 includes deeming that a ventricular tachyarrhythmia is unstable based on a combination of a measurement of hemodynamic stability from the heart sound signal and an indication of unstable ventricular tachyarrhythmia obtained from an electrical cardiac signal. In an example, the method 1100 includes establishing a baseline measurement for a measurement of hemodynamic stability from the heart sound signal and determining a measure of variability of ventricular time intervals. The ventricular tachyarrhythmia is deemed to be unstable when both a measured change from the baseline measurement of hemodynamic stability exceeds a predetermined stability measurement threshold value and the measure of variability of ventricular time intervals exceeds a predetermined variability threshold value.

In some examples, at 1120 the method 1100 includes delaying delivery of a predetermined shock stimulus according to the measurement of hemodynamic stability. If the measurement of hemodynamic stability indicates that the ventricular tachyarrhythmia is stable, the IMD may delay providing such a stimulus. This gives the ventricular tachyarrhythmia time to spontaneously convert to a normal rhythm. This may reduce the number of shocks given to a patient, thereby improving patient comfort and extending the battery life of the IMD.

In some examples, the method 1100 includes initiating a predetermined anti-tachyarrhythmia pacing (ATP) regimen upon detecting the episode of ventricular tachyarrhythmia. If the measurement of hemodynamic stability from the heart sound signal indicates that the tachyarrhythmia is stable, the duration of the ATP regimen is extended. This gives the ATP regimen time to convert the ventricular tachyarrhythmia to a normal rhythm. This also may reduce the number of shocks given to a patient.

Figure 12:
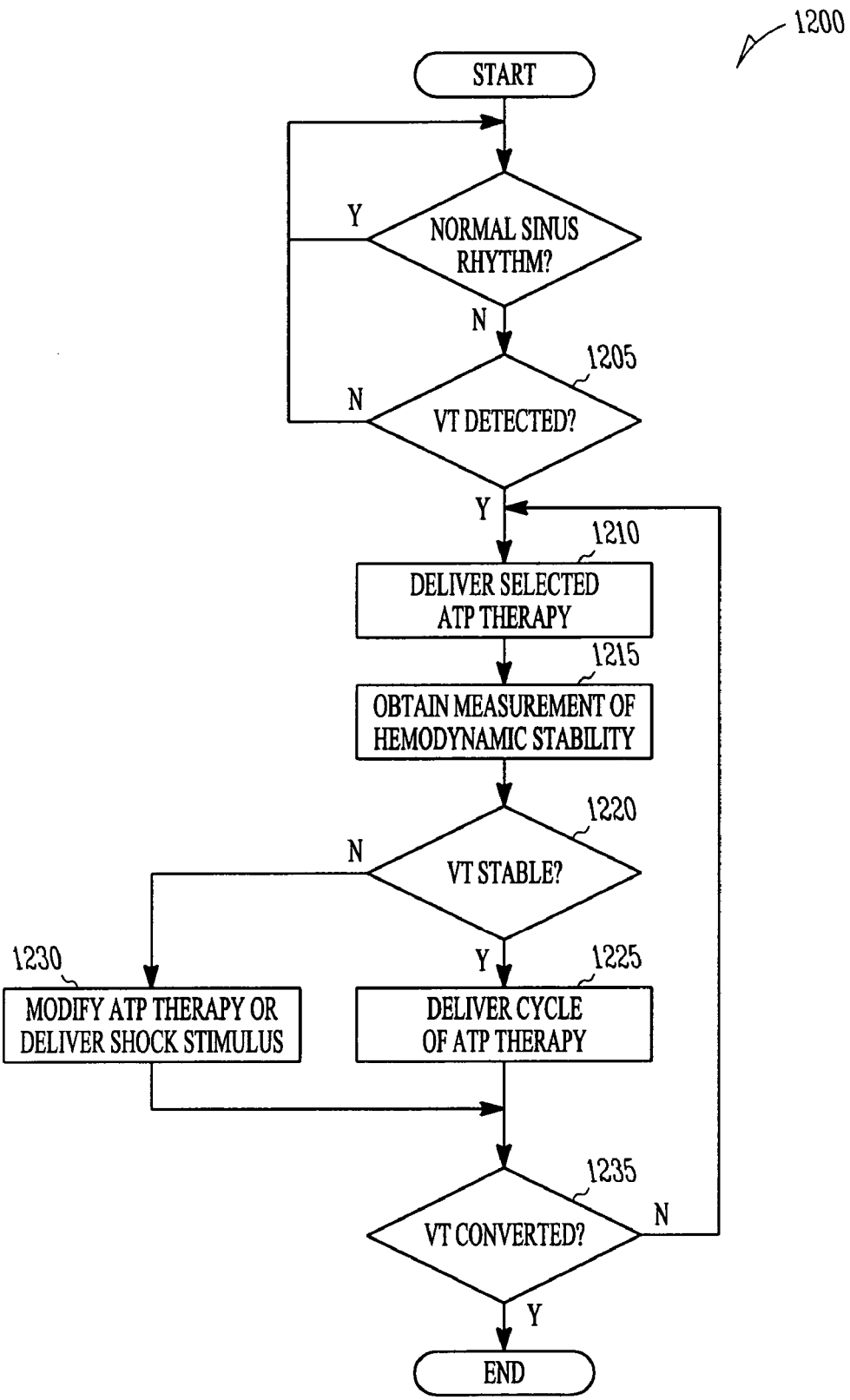
FIG. 12 shows a block diagram of a method that extends an ATP therapy regimen that is provided by an IMD.

FIG. 12 shows a block diagram of a method 1200 that extends an ATP therapy regimen that is provided by an IMD. At 1205, the method includes checking for ventricular tachyarrhythmia. At 1210, a regimen of ATP therapy is selected and delivered. At 1215, a measurement of hemodynamic stability is obtained from a heart sound signal. At 1220, it is determined whether the ventricular tachyarrhythmia is stable using the measurement of hemodynamic stability or using both a measurement of hemodynamic stability and an indication of unstable ventricular tachyarrhythmia obtained from an electrical cardiac signal. Typically, the measurement of hemodynamic stability is obtained on a beat-by-beat basis. If the ventricular tachyarrhythmia is stable, another cycle of the ATP regimen is delivered at 1225. If the ventricular tachyarrhythmia is indicated to be unstable, either a different ATP therapy regimen is chosen and delivered, or a shock stimulus is provided at 1230 to convert the ventricular tachyarrhythmia to a normal sinus rhythm. At 1235 the method ends if the ventricular tachyarrhythmia is converted to normal sinus rhythm, otherwise the IMD continues the ATP regimen while monitoring whether the ventricular tachyarrhythmia remains stable using the measurement of hemodynamic stability.

The systems and methods described herein use hemodynamic information, such as a heart sound proxy for blood pressure within the heart chambers, to improve the likelihood that the device will make a proper assessment of heart rhythm stability. A proper assessment makes it possible to delay the onset of treatment or to extend the time to attempt to resolve the episode with ATP before resorting to high-energy shock therapy. This results in a reduced number of necessary shocks while ensuring that a high-energy shock stimulus will convert the abnormal rhythm if the rhythm fails to convert spontaneously or fails to convert after ATP. Reducing the number of shocks given to a patient improves patient comfort and extends the implantable life of the IMD by reducing the energy required for patient treatment.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   an implantable medical device (IMD) comprising:
   an implantable heart sound sensor operable to produce an electrical signal representative of at least one heart sound, the heart sound associated with mechanical activity of a patient's heart;
   a heart sound sensor interface circuit coupled to the heart sound sensor to produce a heart sound signal;
   a tachyarrhythmia detector; and
   a controller circuit coupled to the heart sound sensor interface circuit and the tachyarrhythmia detector, wherein the controller circuit includes a hemodynamic stability assessment module configured to:
     determine that at least one episode of ventricular tachyarrhythmia is detected in a subject;
     initiate, in response to and obtain during the detected episode of tachyarrhythmia, a measurement of hemodynamic stability of the ventricular tachyarrhythmia from the heart sound signal, wherein the measurement of hemodynamic stability is determined using linear prediction; and
     deem whether the ventricular tachyarrhythmia is stable according to the measurement of hemodynamic stability.

2. The system of claim 1, wherein the hemodynamic stability assessment module includes a baseline module to establish a baseline for the measurement of hemodynamic stability obtained from the heart sound signal; and
   wherein the hemodynamic stability assessment module is further configured to deem the ventricular tachyarrhythmia to be unstable when a measured change from the baseline measurement of hemodynamic stability exceeds a predetermined threshold value.

3. The system of claim 2, wherein the baseline module is configured to establish a baseline for the measurement of hemodynamic stability by determining a central tendency of the measurement of hemodynamic stability.

4. The system of claim 2, wherein the hemodynamic stability assessment module is configured to deem the ventricular tachyarrhythmia to be unstable when a measured change from the baseline measurement of hemodynamic stability exceeds a predetermined threshold value in X of Y consecutive cardiac cycles, wherein X and Y are integers and Y>X.

5. The system of claim 1, wherein the system further includes a timer circuit coupled to the controller circuit to provide a ventricular time interval between ventricular contractions;
   wherein the hemodynamic stability assessment module includes a ventricular contraction variability module to obtain a measure of variability of ventricular time intervals;
   wherein the hemodynamic stability module includes a baseline module to establish a baseline for the measurement of hemodynamic stability obtained from the heart sound signal; and
   wherein the hemodynamic stability assessment module is further configured to deem the ventricular tachyarrhythmia to be unstable when both a measured change from the baseline measurement of hemodynamic stability exceeds a predetermined stability measurement threshold value and the measure of variability of ventricular time intervals exceeds a predetermined variability threshold value.

6. The system of claim 1, wherein the system further includes a shock circuit coupled to the controller circuit, and
   wherein the controller circuit is configured to delay delivery of a predetermined shock stimulus during the detected episode of tachyarrhythmia according to the measurement of hemodynamic stability obtained by the hemodynamic stability assessment module.

7. The system of claim 1, wherein the system further includes an anti-tachyarrhythmia pacing (ATP) circuit coupled to the controller circuit, and wherein the controller circuit is configured to:
   initiate a predetermined ATP regimen upon detecting the episode of ventricular tachyarrhythmia; and
   extend a duration of the ATP regimen during the detected episode of tachyarrhythmia according to the measurement of hemodynamic stability.

8. The system of claim 1, including at least one implantable cardiac signal sensing circuit coupled to the controller circuit, the implantable cardiac signal sensing circuit configured to produce an electrical cardiac signal representative of cardiac activity of the patient, and wherein the hemodynamic stability assessment module is configured to obtain the measurement of hemodynamic stability from a heart sound signal in correlation with the electrical cardiac activity signal.

9. The system of claim 1, including a patient activity sensor coupled to the controller circuit, wherein the hemodynamic stability assessment module is configured to obtain the measurement of hemodynamic stability from a heart sound signal in correlation with patient activity.

10. The system of claim 1, wherein the heart sound sensor interface circuit includes:
   a lowpass filter circuit; and
   a pre-emphasizing circuit to add signal gain to higher frequencies of a lowpass filtered heart sound signal.

11. The system of claim 1, including an external device, and wherein the IMD includes a communication circuit coupled to the controller circuit and the IMD is configured to communicate to an external device information about at least one measurement of hemodynamic stability obtained from a heart sound signal.

12. The system of claim 11, wherein the external device is an IMD programmer.

13. The system of claim 11, wherein the external device is a server in communication with a network, and wherein the server is configured to communicate with the IMD via a third device.

14. The system of claim 11, wherein the external device generates an alarm based on the information about the measurement of hemodynamic stability.

15. The system of claim 1, including a timer circuit, coupled to the tachyarrhythmia detector, to provide a ventricular time interval between ventricular contractions; and
   wherein the tachyarrhythmia detector is configured to declare that a tachyarrhythmia has occurred when an average ventricular contraction rate exceeds an average atrial contraction rate by more than a specified rate threshold value.

16. The system of claim 1, wherein the measurement of hemodynamic stability includes a hemodynamic parameter He, wherein $He = 1 - k_1^2$, $$k_1 = -\left(\frac{R_1}{R_0}\right), \quad R_0 = \sum_{n=0}^{N-1} s_n^2, \text{ and } R_1 = \sum_{n=0}^{N-2} s_n s_{n+1},$$

where $s_n$ are digitized samples of the heart sound signal obtained during a measured heart sound.

17. The system of claim 1, wherein the heart sound sensor includes at least one of an accelerometer, a strain gauge, and a microphone.

* * * * *